US010773055B2

(12) United States Patent
Khalaj et al.

(10) Patent No.: US 10,773,055 B2
(45) Date of Patent: Sep. 15, 2020

(54) ECHOGENIC CATHETER MEMBER

(71) Applicant: Avent, Inc., Alpharetta, GA (US)

(72) Inventors: Steve S. Khalaj, Laguna Hills, CA (US); Kenneth C. Hsu, Tustin, CA (US); Baotram Nguyen Pham, Irvine, CA (US); John Anthony Rotella, San Diego, CA (US); Justin Jeffrey Coker, Laguna Niguel, CA (US); Paul Jun, La Crescenta, CA (US); Kunal Mahendra Amin, La Mirada, CA (US)

(73) Assignee: Avent, Inc., Alpharetta, GA (US)

( * ) Notice: Subject to any disclaimer, the term of this patent is extended or adjusted under 35 U.S.C. 154(b) by 165 days.

(21) Appl. No.: 15/735,731

(22) PCT Filed: Jun. 18, 2015

(86) PCT No.: PCT/US2015/036365
§ 371 (c)(1),
(2) Date: Dec. 12, 2017

(87) PCT Pub. No.: WO2016/204760
PCT Pub. Date: Dec. 22, 2016

(65) Prior Publication Data
US 2018/0177980 A1    Jun. 28, 2018

(51) Int. Cl.
*A61M 25/01* (2006.01)
*A61B 8/08* (2006.01)
(Continued)

(52) U.S. Cl.
CPC ....... *A61M 25/0108* (2013.01); *A61B 8/0841* (2013.01); *A61B 90/36* (2016.02);
(Continued)

(58) Field of Classification Search
CPC ............ A61M 25/0108; A61M 25/007; A61M 25/0606; A61M 2205/3653;
(Continued)

(56) References Cited

U.S. PATENT DOCUMENTS 4,697,595 A    10/1987  Breyer et al.
4,969,890 A    11/1990  Sugita et al.
(Continued)

FOREIGN PATENT DOCUMENTS

EP    2 343 098 A1    7/2011
EP    2 540 336 A1    1/2013
(Continued)

OTHER PUBLICATIONS

Stephen M. Klein, M.D., et al., "Piezoelectric Vibrating Needle and Catheter for Enhancing Ultrasound-Guided Peripheral Nerve Blocks", Technical Communication from the International Anesthesia Research Society, vol. 105, No. 6, Dec. 2007, 3 pages.
(Continued)

*Primary Examiner* — Amber R Stiles
(74) *Attorney, Agent, or Firm* — Dority & Manning, P.A.

(57) ABSTRACT

The present invention is directed to an echogenic member assembly for use with a catheter assembly. The echogenic member assembly includes at least one echogenic member having a cylindrical body extending between a first end and a second end. Thus, the body defines a longitudinal length between the first and second ends. Further, the cylindrical body has an exterior surface extending from the first end to the second end. The exterior surface includes a plurality of discontinuities arranged in a predetermined pattern so as to enhance ultrasonic imaging. In addition, the longitudinal length of the echogenic member is less than a total length of a catheter of the catheter assembly. As such, the echogenic member provides enhanced ultrasonic imaging to the cath-
(Continued)

eter assembly without compromising the inherent flexibility of the catheter.

15 Claims, 10 Drawing Sheets

(51) Int. Cl.
    *A61M 25/06*     (2006.01)
    *A61B 90/00*     (2016.01)
    *A61M 25/00*     (2006.01)
    *A61N 1/05*     (2006.01)

(52) U.S. Cl.
    CPC ...... *A61M 25/007* (2013.01); *A61M 25/0606* (2013.01); *A61B 2090/3925* (2016.02); *A61M 25/0054* (2013.01); *A61M 2205/3653* (2013.01); *A61N 1/05* (2013.01)

(58) Field of Classification Search
    CPC .. A61M 25/0054; A61B 8/0841; A61B 90/36; A61B 2090/3925; A61N 1/05
    See application file for complete search history.

(56) References Cited

U.S. PATENT DOCUMENTS

| | | | |
|---|---|---|---|
| 5,081,997 A | 1/1992 | Bosley, Jr. et al. | |
| 5,759,154 A * | 6/1998 | Hoyns | A61B 8/0833 29/DIG. 16 |
| 6,179,809 B1 * | 1/2001 | Khairkhahan | A61M 25/0084 604/528 |
| 6,306,094 B1 * | 10/2001 | Joseph | A61B 8/481 600/458 |
| 6,860,856 B2 * | 3/2005 | Ward | A61B 90/39 600/459 |
| 7,438,711 B2 | 10/2008 | Deniega et al. | |
| 7,465,291 B2 | 12/2008 | Massengale | |
| 7,527,609 B2 | 5/2009 | Deniega et al. | |
| 7,569,045 B2 | 8/2009 | Denieoa et al. | |
| 8,328,771 B2 | 12/2012 | Massengale | |
| 8,611,993 B2 | 12/2013 | Vitullo et al. | |
| 8,652,098 B2 | 2/2014 | Haslinger | |
| 8,796,908 B2 | 8/2014 | Okuba | |
| 9,802,025 B2 | 10/2017 | Khalaj | |
| 2002/0142119 A1 | 10/2002 | Seward et al. | |
| 2004/0077948 A1 | 4/2004 | Violante et al. | |
| 2004/0116896 A1 | 6/2004 | Massengale | |
| 2004/0193109 A1 | 9/2004 | Prestidge et al. | |
| 2004/0249288 A1 * | 12/2004 | Ichikawa | A61B 10/0233 600/464 |
| 2007/0167739 A1 | 7/2007 | Salo | |
| 2008/0058702 A1 | 3/2008 | Arndt et al. | |
| 2009/0131910 A1 * | 5/2009 | Webler | A61B 8/0841 604/523 |
| 2011/0172542 A1 | 7/2011 | Racz | |
| 2012/0059308 A1 | 3/2012 | Hsu et al. | |
| 2012/0095404 A1 | 4/2012 | Massengale et al. | |
| 2012/0126663 A1 | 5/2012 | Jenninger et al. | |
| 2013/0223702 A1 | 8/2013 | Holsing et al. | |
| 2014/0024928 A1 | 1/2014 | Boctor et al. | |
| 2014/0142509 A1 | 5/2014 | Bonutti et al. | |
| 2014/0316327 A1 | 10/2014 | Rajendran et al. | |
| 2014/0378841 A1 | 12/2014 | Coats et al. | |
| 2015/0038378 A1 | 2/2015 | Cheng et al. | |

FOREIGN PATENT DOCUMENTS

| | | |
|---|---|---|
| JP | 2001293091 A | 10/2001 |
| JP | 2010279546 A | 12/2010 |
| WO | WO 99/51294 | 10/1999 |
| WO | WO 00/04287 | 7/2000 |
| WO | WO 2009/091514 A2 | 7/2009 |
| WO | WO 2014/174305 A2 | 10/2014 |

OTHER PUBLICATIONS

Co-pending U.S. Appl. No. 15/735,719, filed Dec. 12, 2017.
Co-pending U.S. Appl. No. 15/743,900, filed Jan. 11, 2018.
International Search Report for PCT/US2015/036365, dated Nov. 3, 2016, 3 pages.

* cited by examiner

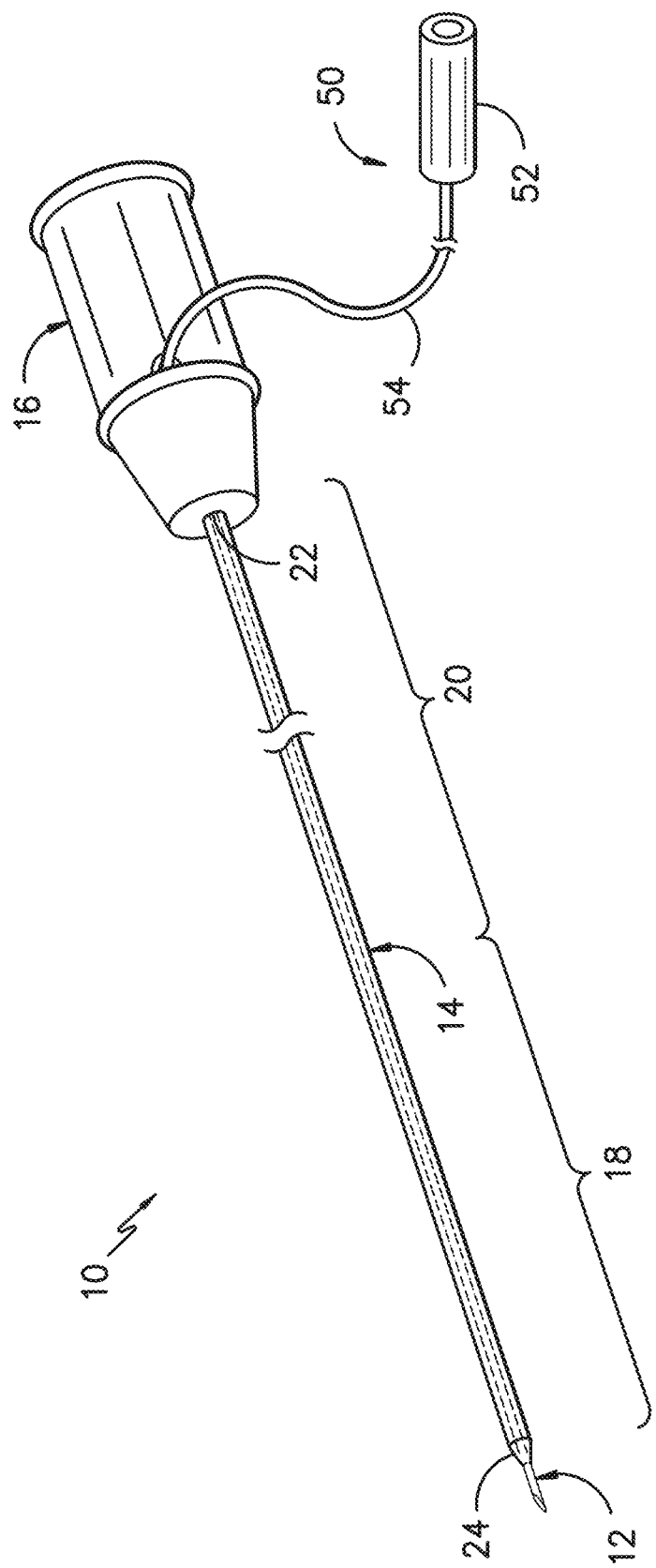
FIG. -1-

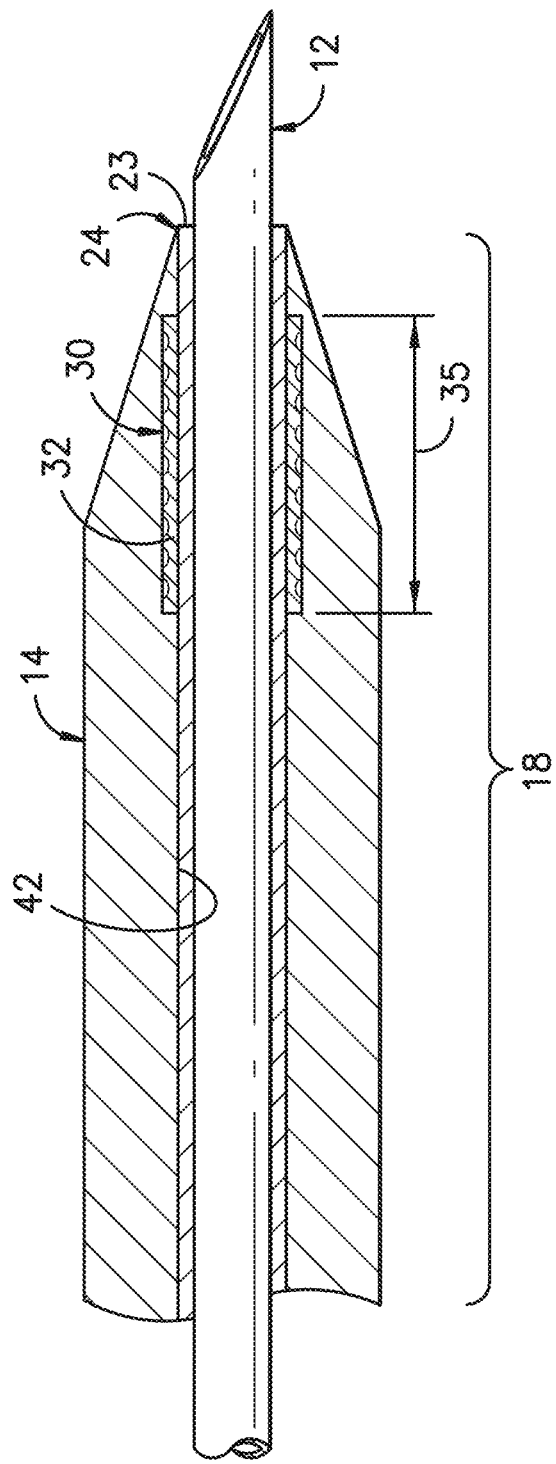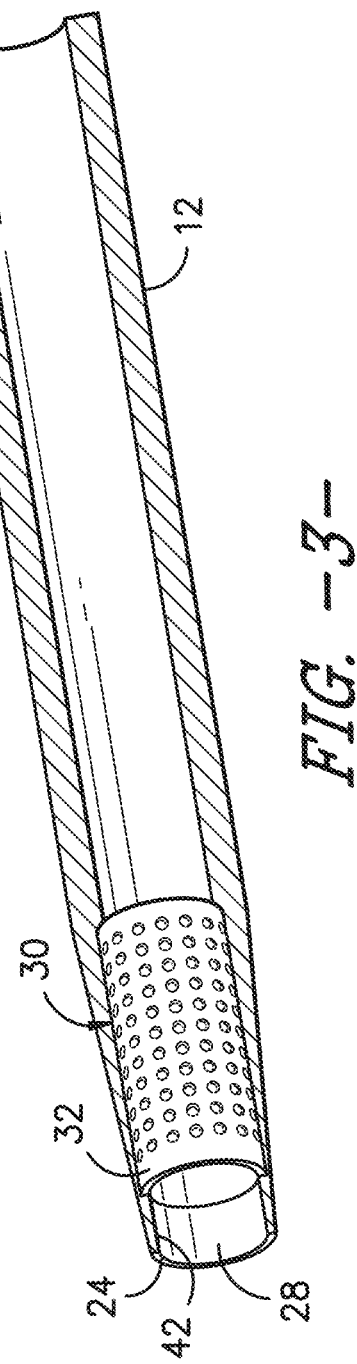

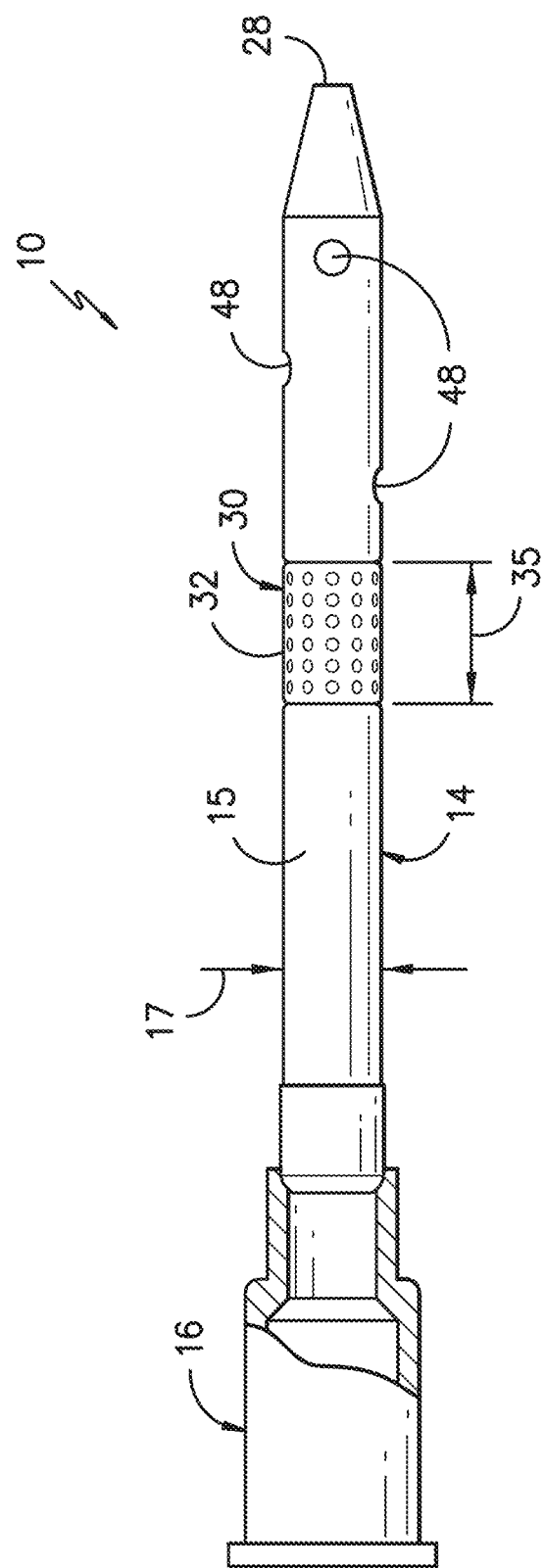
FIG. -4-

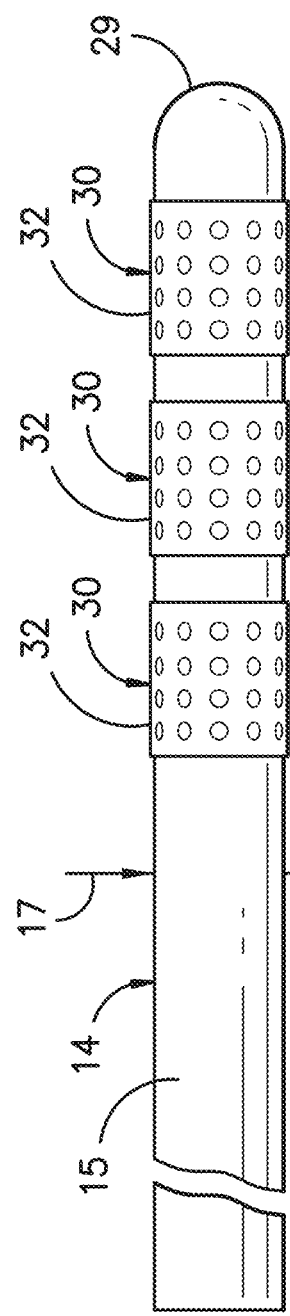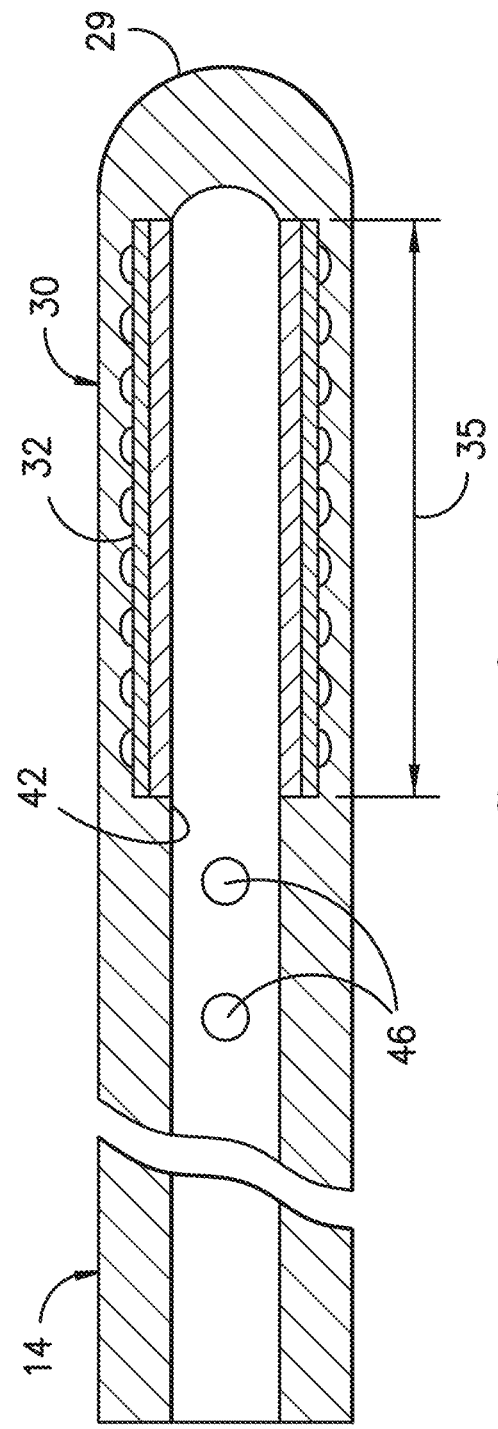

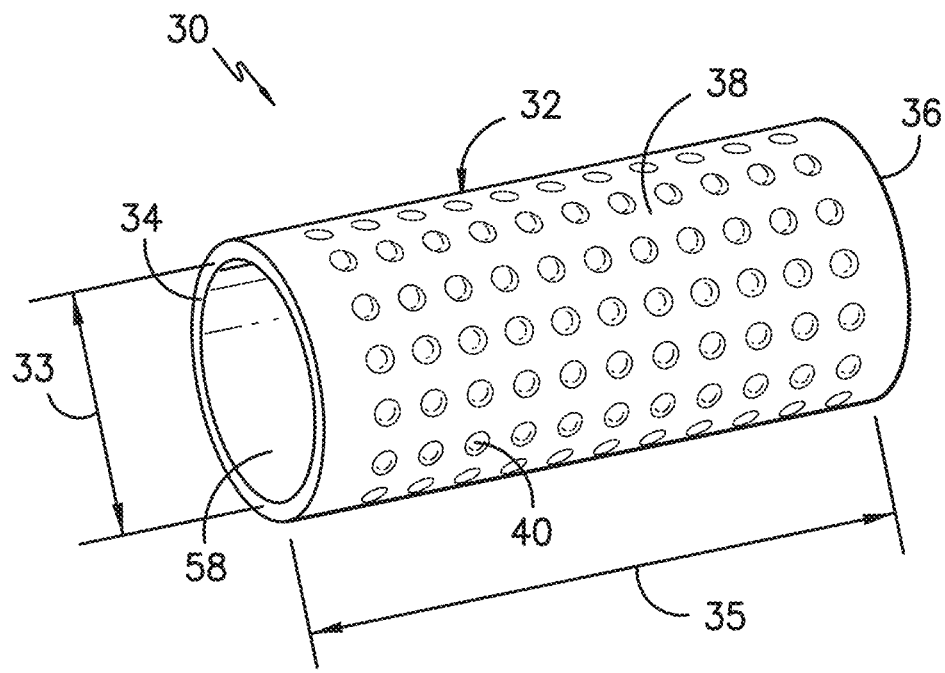
FIG. -7-
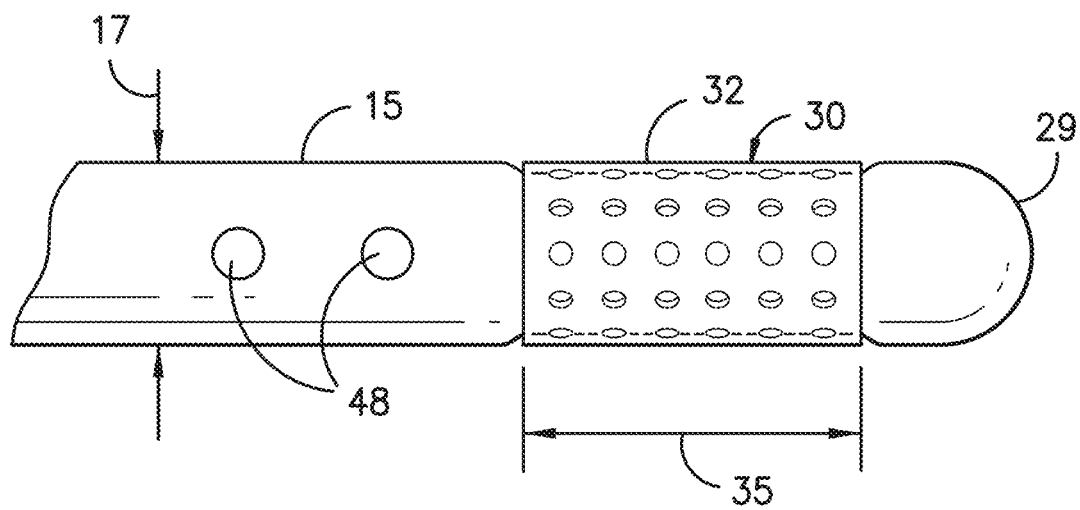
FIG. -8-

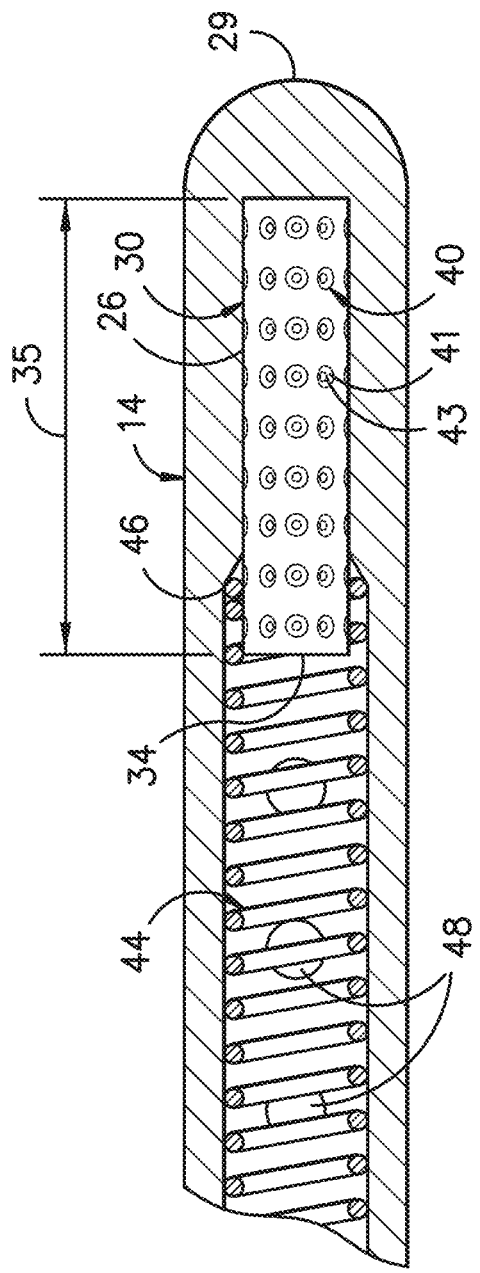
FIG. -9-
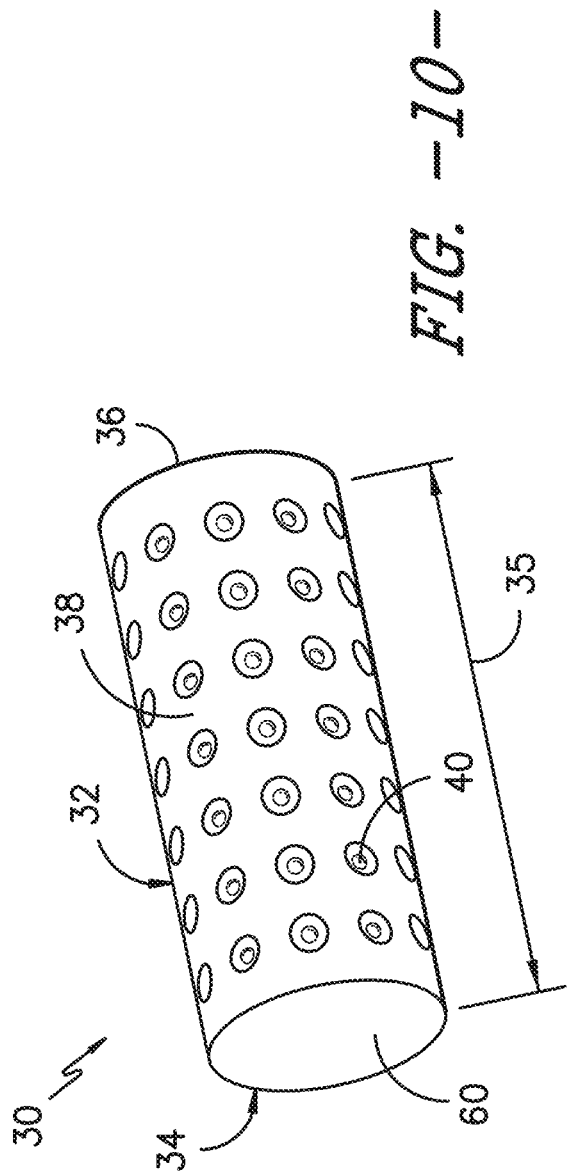
FIG. -10-

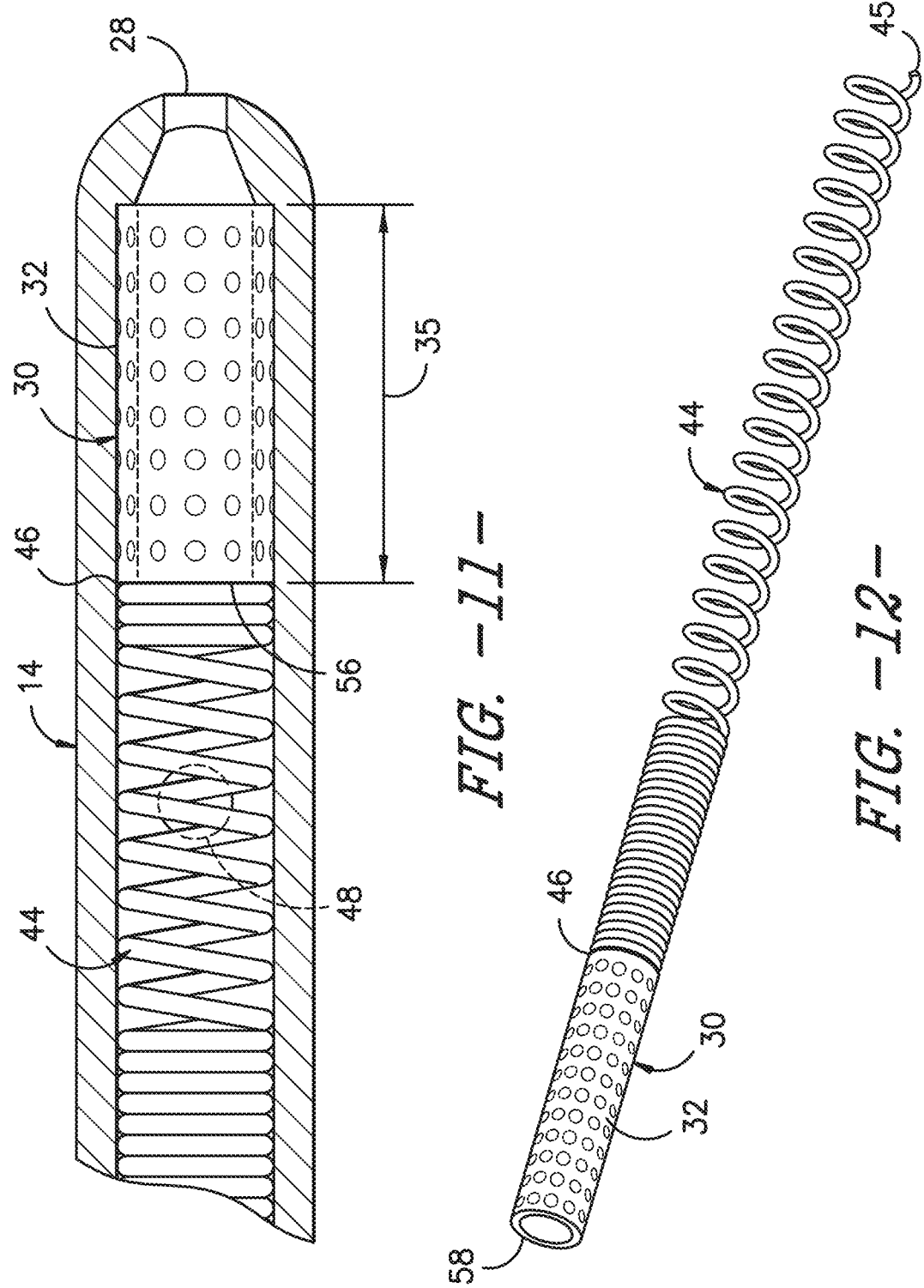
FIG. -11-
FIG. -12-

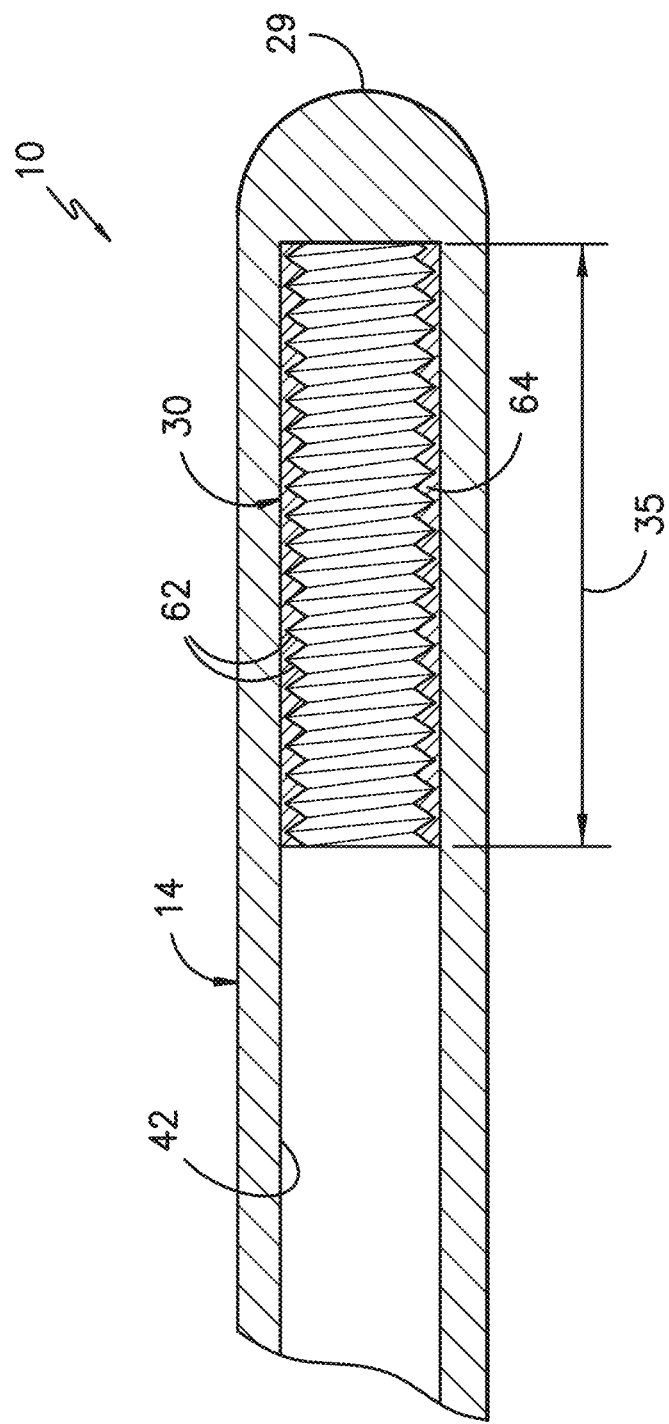

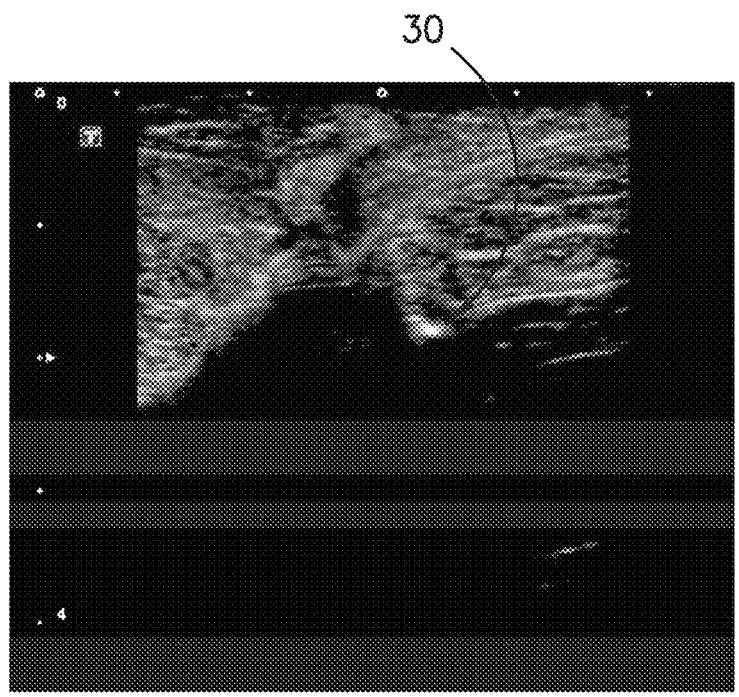
FIG. -14-
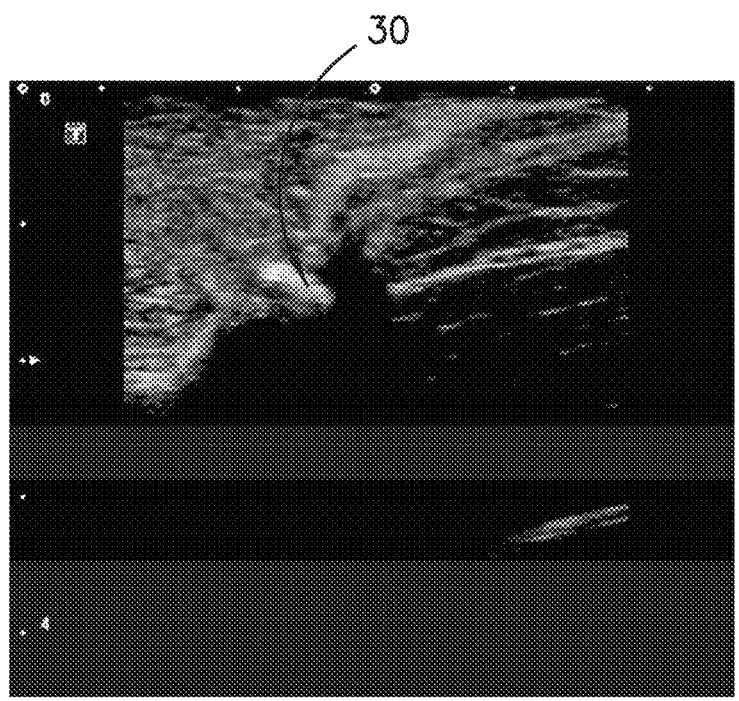
FIG. -15-

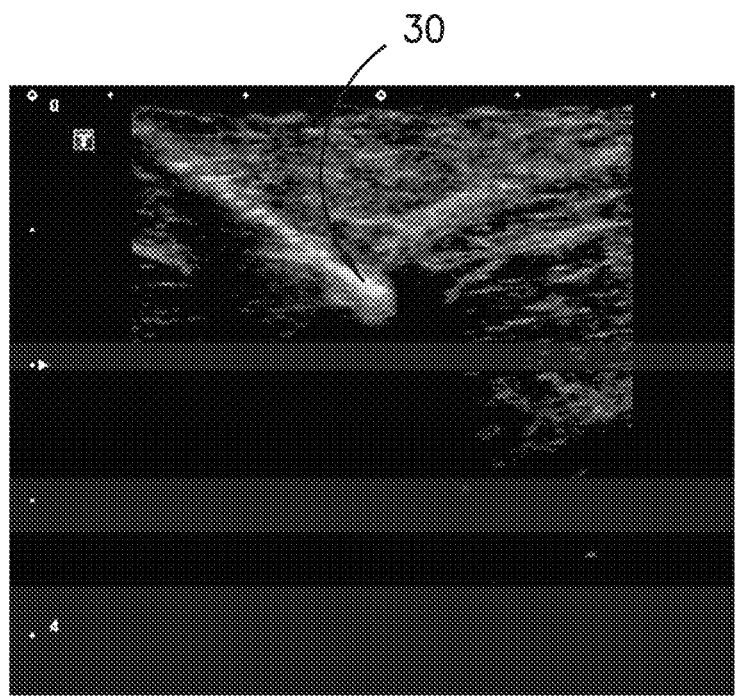
FIG. -16-
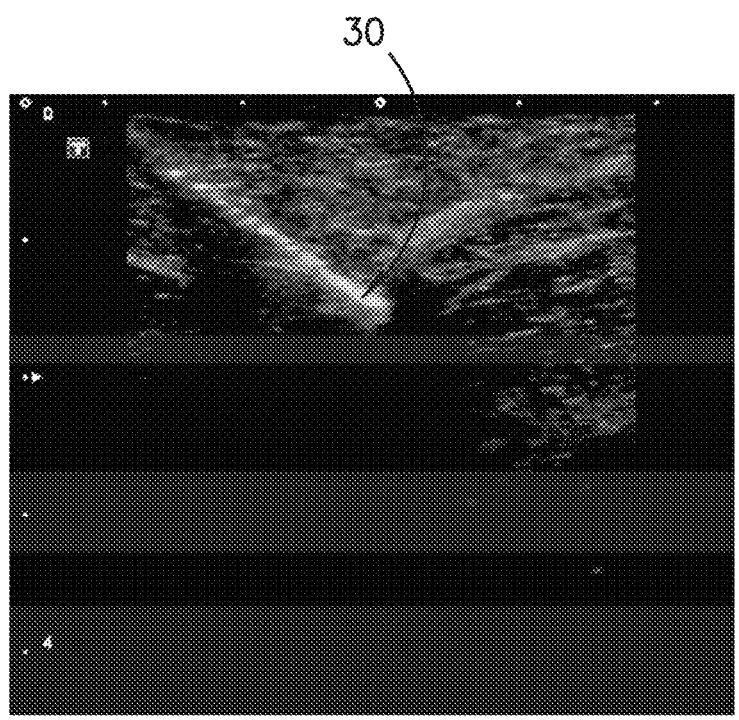
FIG. -17-

ECHOGENIC CATHETER MEMBER

RELATED APPLICATIONS

The present application claims priority to International Application Number PCT/US2015/036365 filed on Jun. 18, 2015, which is incorporated herein in its entirety by reference hereto.

FIELD OF THE INVENTION

The present invention relates generally to echogenic devices and more particularly to an echogenic catheter member that may be used with medical devices that are insertable into a medium such as biological tissue and imageable with sonic imaging equipment.

BACKGROUND

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. The types of devices which are surgically sterilized and inserted into patients are many. Typical examples include: needles, catheters and a variety of other medical products such as stents, dilators, pacing leads, introducers, angiography devices, angioplasty devices, pacemakers, in-patient appliances such as pumps and other devices. Various approaches have been used to enhance ultrasonic imaging by modifying the reflective surface characteristics of these devices.

U.S. Pat. No. 5,081,997 to Bosley, Jr. et al, for "Echogenic Devices, Material and Method" discloses a device such as a needle that includes an interface having a shape that is formed with a dimension that is less than a wavelength of the incident sonic beam. According to Bosley, Jr. et al., the shape includes a dimension such as a radius of curvature which is much less than the wavelength of the sonic beam. The interface may include the outside surface a device or article or material. That surface has a plurality of partially spherical discontinuities for producing a scattered component of the image in response to the incident beam. This image is produced regardless of the incident beam angle of which conventional devices depend for producing a reflected or constructive interference image. The scattered component of the image is produced when the radius of the partially spherical discontinuities or a dimension of another geometric shape or surface are much less than the wavelength of the incoming sonic beam.

U.S. Patent Application Publication No. 2004/0249288 A1 to Ichikawa for "Ultrasonic Puncture Needle" discloses a device including an array of doughnut shaped recesses having a center portion remaining as a protrusion. According to U.S. Publication No. 2004/0249288 A1, the recesses are also formed with faces, bottoms and sides being generally flat so to obtain reflection echoes with a great intensity for the incident ultrasonic waves with a shallow incident angle.

While the approaches described in U.S. Pat. No. 5,081,997 and U.S. Publication No. 2004/0249288 A1 have shown promise, improvements have been sought that would result in an echogenic catheter that provides enhanced ultrasonic imaging, in a manner that is inexpensive to manufacture, and simple and reliable to use.

Accordingly, the present disclosure is directed to an echogenic member for a catheter assembly that provides enhanced ultrasonic imaging without compromising the inherent flexibility of the catheter.

SUMMARY OF THE INVENTION

Objects and advantages of the invention will be set forth in part in the following description, or may be obvious from the description, or may be learned through practice of the invention.

In one aspect, the present invention is directed to an echogenic over-the-needle (OTN) catheter assembly. The catheter assembly includes a catheter having a proximal end and a distal end that defines a lumen extending from the proximal end to the distal end. Further, the catheter assembly includes a needle configured within the lumen of the catheter. Moreover, the catheter assembly includes an echogenic member configured with the catheter. The echogenic member includes a body defining an exterior surface extending between a first end and a second end. Further, the exterior surface includes a plurality of discontinuities configured to enhance ultrasonic imaging.

In one embodiment, the echogenic member is located in a distal region of the catheter. For example, in certain embodiments, the echogenic member may be located at the distal tip of the catheter. In another embodiment, the distal end of the catheter may include an open distal tip, wherein the needle extends past the open distal tip. Further, in certain embodiments, the echogenic member may surround the needle and/or may be embedded into an interior wall of the catheter. Alternatively, the echogenic member may be configured to surround an exterior surface of the catheter.

In alternative embodiments, the catheter assembly may include a coil configured within the lumen of the catheter, wherein the coil extends from a proximal end to a distal end. In such an embodiment, the echogenic member may be secured to the distal end of the coil. In another embodiment, the echogenic member may be sized to fit within the lumen of the catheter and within the distal end of the coil. In additional embodiments, the echogenic member may be secured to the distal end of the coil and embedded to the interior wall of the catheter. Alternatively, the echogenic member may simply fit within the lumen of the catheter rather than being embedded.

For example, in certain embodiments, the coil and the echogenic member may each include a hollow cross-section such that, when arranged together, form a lumen between the proximal end of the catheter to an open distal tip of the catheter. Alternatively, the echogenic member may include a solid cross-section. In such an embodiment, the catheter may include one or more infusion holes configured through the wall of the catheter and a closed distal tip. Thus, the infusion holes allow a medication flowing through the lumen of the catheter (and a lumen created by the coil) to exit therethrough.

In further embodiments, the echogenic catheter assembly may further include a plurality of echogenic members configured with the exterior surface of the catheter and spaced along a longitudinal length of the catheter. More specifically, the spacing of the plurality of echogenic members does not compromise the flexibility of the catheter.

In additional embodiments, the discontinuities of the echogenic member may include any suitable discontinuities (e.g. dimples, recesses, or similar) having any suitable size and/or shape arranged in any suitable pattern so as to provide enhanced ultrasonic imagine. For example, in certain embodiments, the discontinuities may include at least one or more of the following: indentations, grooves, notches, recesses, threads, protrusions, or similar. More specifically, in particular embodiments, the indentations may include flat bottoms and flat sides. In further embodiments, the indentations may include a first spherical indentation and a second spherical indentation contained within the first indentation to enhance ultrasonic imaging. In addition, the pattern of the discontinuities may be organized or random.

In yet another embodiment, the catheter assembly may also include a filler material configured between the echogenic member and an interior wall of the catheter. Thus, the filler material is configured to fill in any voids between an outer surface of the echogenic member (e.g. created by the discontinuities) and the interior wall of the catheter so as to enhance ultrasonic imaging of the echogenic member. More specifically, in certain embodiments, the filler material may have a density of about 0.9 g/cm$^3$ to about 1.1 g/cm$^3$, which is similar to the density of fat and/or muscle tissue, as well as the density of the catheter material.

In still additional embodiments, the echogenic member may be constructed of any suitable material. For example, in specific embodiments, the echogenic member may be constructed of a metal or metal alloy. More particularly, the metal or metal alloy may include at least one of or a combination of the following: aluminum, titanium, copper, tin, nickel, zinc, magnesium, stainless steel, or similar.

In another aspect, the present disclosure is directed to an echogenic catheter assembly. The catheter assembly includes a catheter, an echogenic member, and a filler material. The catheter has a proximal end and a distal end and defines a lumen extending from said proximal end to the distal end. The echogenic member is configured with the distal end of the catheter and includes a body defining an exterior surface extending between a first end and a second end. Further, the exterior surface includes a plurality of discontinuities (e.g. threads). The catheter assembly also includes a filler material configured between the discontinuities of the echogenic member and an interior wall of the catheter so as to enhance ultrasonic imaging of the echogenic member. In one embodiment, the catheter may have a closed distal tip. Alternatively, the catheter may have an open distal tip such that the echogenic member may be used as a plug at the distal tip.

In yet another aspect, the present disclosure is directed to an echogenic member assembly for use with an over-the-needle (OTN) catheter assembly. The echogenic member assembly includes at least one echogenic member. The echogenic member includes a cylindrical body having a first end and a second end defining a longitudinal length therebetween. The cylindrical body defines an exterior surface extending from the first end to the second end. Further, the exterior surface includes a plurality of discontinuities. The discontinuities are arranged in a predetermined pattern so as to enhance ultrasonic imaging. In addition, the longitudinal length of the echogenic member is less than a total length of a catheter of the OTN catheter assembly. As such, the echogenic member provides enhanced ultrasonic imaging to the OTN catheter assembly without compromising the inherent flexibility of the catheter.

In one embodiment, the echogenic member assembly may include a plurality of echogenic members. As such, the plurality of echogenic members can be spaced apart along the total length of the catheter to provide enhanced ultrasonic imaging without compromising the inherent flexibility of the catheter.

In certain embodiments, the echogenic member(s) may be configured to surround a portion of a needle of the OTN catheter assembly. In such an embodiment, the echogenic member(s) may be embedded within an interior wall of the catheter assembly or may simply provide an interference fit with the interior wall of the catheter. Alternatively, the echogenic member(s) may be configured to surround a portion of the catheter of the OTN catheter assembly. In such an embodiment, the catheter may be heated and stretched such that the echogenic member(s) can be easily inserted around the outer diameter of the catheter. Thus, once the catheter cools, the echogenic member(s) remain secure.

In further embodiments, the echogenic member(s) may be configured to fit within a lumen of the catheter and may include a solid cross-section or a hollow cross-section. In addition, it should be understood that the echogenic member (s) of the echogenic member assembly may further include any of the additional features described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of a catheter assembly according to the present disclosure;

FIG. 2 illustrates a cross-sectional view of one embodiment of a catheter assembly according to the present disclosure, particularly illustrating an echogenic member configured within a lumen of the catheter;

FIG. 3 illustrates a perspective view of one embodiment of a catheter assembly according to the present disclosure, particularly illustrating an echogenic member configured within a lumen of the catheter;

FIG. 4 illustrates a side view of one embodiment of a catheter assembly according to the present disclosure, particularly illustrating an echogenic member configured around a catheter of the assembly;

FIG. 5 illustrates a side view of another embodiment of a catheter assembly according to the present disclosure, particularly illustrating a plurality of echogenic members configured around a catheter of the assembly;

FIG. 6 illustrates a cross-sectional view of one embodiment of a catheter assembly according to the present disclosure, particularly illustrating an echogenic member configured within a lumen of a catheter of the assembly;

FIG. 7 illustrates a perspective view of one embodiment of an echogenic member according to the present disclosure;

FIG. 8 illustrates a side view of one embodiment of a catheter assembly according to the present disclosure, particularly illustrating an echogenic member configured around a catheter of the assembly at a distal end thereof;

FIG. 9 illustrates a cross-sectional view of one embodiment of a catheter assembly according to the present disclosure, particularly illustrating an echogenic member configured with a coil of the catheter assembly;

FIG. 10 illustrates a perspective view of another embodiment of an echogenic member according to the present disclosure;

FIG. 11 illustrates a cross-sectional view of another embodiment of a catheter assembly according to the present disclosure, particularly illustrating an echogenic member configured with a distal end of a coil of the catheter assembly;

FIG. 12 illustrates a partial, perspective view of another embodiment of a catheter assembly according to the present disclosure, particularly illustrating an echogenic member configured with a distal end of a coil of the catheter assembly;

FIG. 13 illustrates a perspective view of yet another embodiment of an echogenic catheter assembly according to the present disclosure; and FIGS. 14-17 illustrate various views of an echogenic member of an echogenic catheter assembly under ultrasonic imaging according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to an echogenic member for use with an over-the-needle (OTN) catheter. The echogenic member includes a cylindrical body having a first end and a second end defining a longitudinal length therebetween. Each cylindrical body defines an exterior surface having a plurality of discontinuities arranged in a predetermined pattern so as to enhance ultrasonic imaging. In addition, the longitudinal length of the echogenic member is less than a total length of a catheter of the OTN catheter assembly so as to maintain the inherent flexibility of the catheter.

Referring now to the drawings, FIG. 1 illustrates one embodiment of an echogenic catheter assembly 10 according to the present disclosure. For example, as shown, the catheter assembly 10 includes catheter 14 having a proximal end 22 and distal end 24 coaxially mounted onto a needle 12. Thus, the catheter assembly 10 is configured such that the catheter 14 and needle 12 can be simultaneously inserted into a patient. In addition, the catheter 14 (and/or the needle 12) defines a lumen 26 extending from the proximal end 22 to the distal end 24 of the catheter 14. Thus, the catheter 14 is configured to deliver a treatment fluid to a targeted site within the patient via the lumen 26. More specifically, in certain embodiments, the proximal end 22 of the catheter 14 may include a hub 16 configured thereon for mating communication with a fluid delivery device (not shown) such that a treatment fluid can be delivered to a targeted site within a patient via the lumen 26 of the catheter 14. As mentioned, the fluid delivery device may be any suitable device known in the art, such as a pump, reservoir, syringe, or the like. Further, the hub 16 may have any conventional configuration, such as a Luer-lock fitting. Thus, in various embodiments, the catheter assembly 10 may include one or more infusion holes 48 along an exterior surface 15 of the catheter 14 and/or a closed 29 or open 28 distal tip, depending on the desired delivery application of the treatment fluid to the patient.

In addition, the echogenic catheter assembly 10 may also include a heat application assembly 50 configured to apply heat to the catheter 14. For example, as shown in FIG. 1, the heat application assembly 50 may be coupled with the hub 16 of the catheter 14 so as to apply heat or current to the catheter 14. In further embodiments, the heat application assembly 50 may be directly coupled to the catheter 14 or the needle 12 or any other suitable component of the catheter assembly 10. Further, as shown in FIG. 1, the heat application assembly 50 may correspond to a nerve stimulator apparatus having a nerve stimulator 52 that provides heat or current through one or more stimulator wires 54. It should be understood, however, that the heat application assembly 50 can further include any other suitable heating assembly known in the art and the illustrated embodiment is provided for illustrative purposes only. For example, in further embodiments, the heat application assembly 50 may also include one or more battery devices, temperature-controlled water, an ultrasound device, a vibration device, or similar.

Referring now to FIGS. 2-13, various views of the echogenic catheter assembly 10 having at least one echogenic member 30 according to the present disclosure are illustrated. As shown generally in the figures, the echogenic member 30 may include a cylindrical body 32 defining an exterior surface 38 extending between a first end 34 and a second end 36. Thus, the body 32 of the echogenic member 30 defines a total longitudinal length 35 extending between the first end 34 and the second end 36. In certain embodiments, the longitudinal length 35 of the echogenic member 30 may be less than a total length of the catheter 14. Thus, in such embodiments, the echogenic member 30 does not compromise the flexibility of the catheter 14. In addition, the exterior surface 38 may include a plurality of discontinuities 40 configured to enhance ultrasonic imaging. For example, in certain embodiments, the discontinuities 40 may be arranged in a predetermined pattern so as to enhance ultrasonic imaging. In one embodiment, the predetermined pattern may include organized rows and/or columns of discontinuities. Alternatively, the pattern of discontinuities 40 may be random.

It should be understood that certain embodiments of the catheter assembly 10 may include one echogenic member 30, for example, located in the distal region 18 of the catheter 14 as shown in FIGS. 2-4, 6, 8-9, and 11-12. In alternative embodiments, as shown in FIG. 5, the echogenic catheter assembly 10 may include a plurality of echogenic members 30 configured with the catheter 14. More specifically, as shown, the plurality of echogenic members 30 may be configured with the exterior surface 15 of the catheter 14 and spaced along a longitudinal length of the catheter 14. In alternative embodiments, the plurality of echogenic members 30 may be configured within the lumen 26 of the catheter 14 and spaced along the length thereof. Thus, for each of the embodiments described herein, the echogenic member(s) 30 provides enhanced ultrasonic imaging to the catheter assembly 10 without compromising the inherent flexibility of the catheter 14.

In additional embodiments, the discontinuities 40 of the echogenic member(s) 30 may include any suitable discontinuities having any suitable size and/or shape arranged in any suitable pattern so as to provide enhanced ultrasonic imagine. For example, in certain embodiments, the discontinuities 40 may include at least one or more of the following: indentations, grooves, notches, recesses, threads, protrusions, or similar. In addition, as mentioned the pattern of the discontinuities 40 may be organized or random. More particularly, as shown in generally in FIGS. 2-8, the discontinuities 40 may include flat bottoms and flat sides. In further embodiments, as shown in FIGS. 9 and 10, the discontinuities 40 may include a first spherical indentation 41 and a second spherical indentation 43 contained within the first indentation 41 to enhance ultrasonic imaging. For example, U.S. Patent Application Publication No.: 2014/0378841 entitled "Echogenic Article with Compound Discontinuities" filed on Jun. 18, 2014 discloses suitable discontinuities that may be included on the echogenic member 30 of the present disclosure and is herein incorporated by reference in its entirety. In still further embodiments, as shown in FIG. 13, the discontinuities 40 may include threads 62. More particularly, the threads 62 may include longitudinal or radial threads. For example, in a specific embodiment, the echogenic member 30 may be a stainless steel screw size 0000-160 Unified Miniature Screw Threads with 0.021" major diameter. In addition and still referring to FIG. 13, the catheter assembly 10 may also include a filler material 64 configured between the echogenic member 30 (e.g. created by the discontinuities 40) and the interior wall 42 of the catheter 14. In certain situations, air within the catheter 14 can dampen the sound waves and mitigate the echogenicity of the echogenic member 30. Thus, the filler material 64 is configured to fill in any voids between an outer surface of the echogenic member 30 and the interior wall 42 of the catheter 14 so as to enhance ultrasonic imaging of the echogenic member. As such, the filler material 63 can be any suitable liquid medium (e.g. saline, water, Loctite, etc.) suitable for filling the voids/air space within the catheter assembly 10. More specifically, in certain embodiments, the filler material 63 should desirably have a density that is similar to the density of fat and/or muscle tissue as well as the catheter 14 (e.g. from about 0.9 $g/cm^3$ to about 1.1 $g/cm^3$, more preferably about 1 $g/cm^3$). Thus, the filler material 63 effectively eliminates void space that provides a large difference in density—causing attenuation of ultrasonic waves or that may alter reflectivity. It should also be understood that the filler material 63 may be used with any over-the-needle (OTN) catheters as well as any other suitable type of catheter, with or without the use of a needle, that utilize the echogenic band(s) 30 as described herein.

In further embodiments, the discontinuities 40 of the echogenic member(s) may be manufactured using any suitable means. For example, in certain embodiments, the discontinuities 40 may be manufactured using laser etching, spatter techniques (i.e. displacement of metal and/or other phenomena), cutting, machining, or similar. In still additional embodiments, the echogenic member 30 may be constructed of any suitable echogenic material. For example, in specific embodiments, the echogenic member 30 may be constructed of a metal or metal alloy. More particularly, the metal or metal alloy may include at least one of or a combination of the following: aluminum, titanium, copper, tin, nickel, zinc, magnesium, stainless steel, or similar.

It should be understood that the echogenic member 30 described herein may be located at any suitable location of the catheter assembly 10 so as to provide enhanced ultrasonic imaging. For example, as shown in FIGS. 2 and 3, the echogenic member 30 may be configured within the lumen 26 of the catheter 14. Further, as shown, the echogenic member 30 may be located in the distal region 18 of the catheter 14, e.g. at or near the distal end 24 of the catheter 14. More particularly, the illustrated embodiment depicts an over-the-needle (OTN) catheter 14 coaxially mounted on the needle 12 which is configured within the lumen 26 of the catheter 14. In such an embodiment, the distal end 24 of the catheter 14 may include an open distal tip 28 such that the needle 12 may be configured to extend past the open distal tip 28 as shown in FIG. 2. In addition, as shown, the echogenic member 30 may be configured to surround the needle 12 within the lumen 26.

Further, as shown particularly in the embodiments of FIGS. 2, 3, and 6, the echogenic member 30 may be embedded into an interior wall 42 of the catheter 14. More specifically, as shown, the echogenic member 30 may be completely embedded within the interior wall 42 such that the diameter of the lumen 26 is unchanged and the needle 12 can easily fit therethrough. In alternative embodiments, the echogenic member 30 may be partially embedded within the interior wall 42 such that the diameter of the lumen 26 is reduced, yet still allows the needle 12 to fit therethrough. Alternatively, the echogenic member 30 may simply be sized to fit within the lumen 26 of the catheter 14, e.g. so as to provide an interference fit between the interior wall 42 of the catheter 14 and the member 30.

Referring now to FIGS. 4, 5, and 8, rather than being inside of the catheter, the echogenic member 30 may also be configured to surround a portion of the catheter 14. In such an embodiment, the inner diameter 33 of the echogenic member 30 may be sized to be slightly larger than the outer diameter 17 of the catheter 14 such that the member 30 can fit securely around the outer diameter 17 of the catheter 14. Alternatively, the inner diameter 33 of the echogenic member 30 may be sized to be slightly smaller than the outer diameter 17 catheter 14. In such an embodiment, the catheter 14 may be heated (e.g. via heat application assembly 50 or any other suitable heating device) and stretched such that the echogenic member(s) 30 can be easily inserted around the outer diameter 17 of the catheter 14. Thus, once the catheter 14 cools, the echogenic member(s) 30 remains secured to the exterior surface 15 of the catheter 14. In still further embodiments, the echogenic member(s) 30 may be segmented such that the member(s) may be easily installed around the outer diameter 17 of the catheter 14.

Referring now to FIGS. 10-12, the catheter assembly 10 may include a coil 44 configured within the lumen 26 of the catheter 14, wherein the coil 44 extends from a proximal end 45 to a distal end 46. In such an embodiment, the nerve stimulator apparatus 50 (FIG. 1) may be configured to apply current through the coil 44 for use during various medical procedures. Thus, it should be understood that the coil 44 may fit within the lumen 26 or may be embedded to the interior wall 42 of the catheter 14. In addition, the echogenic member 30 may be configured with the distal end 46 of the coil 44. More specifically, as shown in FIG. 9, the first end 34 of the echogenic member 30 may be secured at least partially within the coil 44 (which is embedded in the interior wall 42 of the catheter 14). Further, as shown, the echogenic member 30 can be sized to fit within the lumen 26 of the catheter 14. In additional embodiments, as shown in FIG. 11, the echogenic member 30 may be secured to the distal end 46 of the coil 44. For example, in certain embodiments, the echogenic member 30 may be welded to the distal end 46 of the coil 44 at seam 56. In further embodiments, the echogenic member 30 may be secured to the coil 44 using any other suitable means including but not limited to biocompatible adhesives or similar.

In addition, as shown particularly in FIGS. 11 and 12, the coil 44 and the echogenic member 30 may each include a hollow cross-section 58 such that, when arranged together, the coil 44 and the member 30 form a lumen from the proximal end 22 of the catheter 14 to the open distal tip 28 of the catheter 14. In other words, when the coil 44 and the member 30 are configured within the lumen 26, fluids can still flow through the lumen 26 to be delivered to a patient. Alternatively, as shown in FIGS. 9 and 10, the echogenic member 30 may include a solid cross-section 60. In such an embodiment, the echogenic member 30 and closed distal tip 29 of the catheter 14 act as an occluding component at the distal end 24 of the catheter 14. Thus, treatment fluid can exit the one or more infusion holes 48 of the catheter 14 rather than the distal end 24 of the catheter 14.

Referring now to FIGS. 14-17, various views of the echogenic member 30 of the echogenic catheter assembly 10 under ultrasonic imaging according to the present disclosure are illustrated. As shown, the echogenic member 30 is illuminated under ultrasonic imaging. More specifically, in the embodiments of FIGS. 14-17, the catheter 14 of the echogenic catheter assembly 10 may include a Soaker Pebax catheter 19 gage, however, it should be understood that the echogenic catheter assembly 10 as described herein may include any other suitable catheter known in the art. Thus, in certain embodiments, the echogenic members 30 may be installed by cutting the distal end 24 of the catheter 14 and inserting one or more of the members 30 therein. In addition, in the illustrated embodiment, the images were produced with the ultrasound Toshiba Viamo™ although it should be understood that any suitable ultrasound device is configured to generate similar images using the present disclosure.

Thus, as shown generally in FIGS. 14-17, the echogenic member 30 becomes more easily viewed under ultrasonic imaging as the air within the catheter 14 (i.e. between the catheter 14 and the echogenic member 30) is removed. For example, as shown in FIGS. 14 and 15, only a portion of the echogenic member 30 can be seen in the ultrasonic image. Each subsequent image (as shown in FIGS. 16 and 17) illustrates how the echogenic member 30 can be more easily visible as air is reduced and/or eliminated from within the catheter 14, e.g. using the filler material 64 described herein. More specifically, as shown in FIGS. 16 and 17, a user can visualize that the echogenic member 30 is angled at a generally 45-degree angle. Thus, the addition of the filler material 64 between the catheter 14 and the echogenic member 30 eliminates air therefrom such that the air cannot dampen the sound waves which make the catheter assembly 10 harder to see via ultrasonic imaging.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An echogenic over-the-needle (OTN) catheter assembly, comprising:
    a catheter comprising a proximal end and a distal end and defining a lumen extending from said proximal end to said distal end;
    a needle arranged within the lumen of said catheter; and
    an echogenic band embedded into an interior wall of said catheter and surrounding said needle, said echogenic band comprising a body defining an exterior surface extending between a first end and a second end, the exterior surface comprising a plurality of discontinuities configured to enhance ultrasonic imaging,
    wherein each of the plurality of discontinuities comprise an elliptical shape formed on the exterior surface of the body of the echogenic band.

2. The catheter assembly of claim 1, wherein said echogenic band is located in a distal region of said catheter.

3. The catheter assembly of claim 1, wherein said distal end of said catheter comprises an open distal tip, and wherein said needle extends past said open distal tip.

4. The catheter assembly of claim 1, further comprising a coil configured within the lumen of said catheter, wherein said coil extends from a proximal end to a distal end.

5. The catheter assembly of claim 4, wherein said echogenic band is secured to said distal end of said coil.

6. The catheter assembly of claim 5, wherein said coil and said echogenic band each comprise a hollow cross-section such that, when arranged together, said coil and said echogenic band form a lumen between the proximal end of said catheter to an open distal tip of said catheter.

7. The catheter assembly of claim 1, further comprising a plurality of echogenic bands arranged on an exterior surface of said catheter and spaced along a longitudinal length of said catheter.

8. The catheter member of claim 7, wherein said echogenic band is constructed of a metal or metal alloy, wherein the metal or metal alloy comprises at least one of or a combination of the following: aluminum, titanium, copper, tin, nickel, zinc, magnesium, or stainless steel.

9. The catheter assembly of claim 1, wherein the plurality of discontinuities comprises at least one or more of the following: indentations, grooves, notches, recesses, or protrusions.

10. The catheter assembly of claim 1, further comprising a filler material configured between the echogenic band and an interior wall of the catheter, wherein the filler material comprises a density of about 0.9 g/cm3 to about 1.1 g/cm3 so as to enhance ultrasonic imaging of the echogenic band.

11. An echogenic catheter assembly, comprising:
    a catheter comprising a proximal end and a distal end and defining a lumen extending from said proximal end to said distal end;
    an echogenic band embedded into an interior wall of said catheter at said distal end of said catheter, said echogenic band comprising a body defining an exterior surface extending between a first end and a second end, the exterior surface comprising a plurality of discontinuities, each of the plurality of discontinuities comprising an elliptical shape formed on the exterior surface of the body of the echogenic band; and
    a filler material configured between the plurality of discontinuities of the echogenic band and an interior wall of the catheter so as to enhance ultrasonic imaging of the echogenic band.

12. An echogenic member assembly for use with an over-the-needle (OTN) catheter assembly, comprising:
    at least one band comprising a cylindrical body comprising a first end and a second end defining a longitudinal length, said body defining an exterior surface extending from the first end to the second end, the exterior surface comprising a plurality of discontinuities, said plurality of discontinuities being arranged in a predetermined pattern so as to enhance ultrasonic imaging, each of the plurality of discontinuities comprising an elliptical shape formed on the exterior surface of the body of the echogenic band, wherein said longitudinal length of said echogenic band is less than a total length of a catheter of the OTN catheter assembly, wherein said at least one echogenic band is configured to fit within a lumen of the catheter.

13. The echogenic member assembly of claim 12, further comprising a plurality of echogenic bands.

14. The echogenic member assembly of claim 12, wherein said at least one echogenic band configured to surround at least one of a portion of a needle of the OTN catheter assembly or a portion of the catheter of the OTN catheter assembly.

15. The echogenic member assembly of claim 12, wherein the plurality of discontinuities comprises at least one or more of the following: indentations, grooves, notches, recesses, or protrusions.

* * * * *